United States Patent
Bhattacharjee et al.

(10) Patent No.: US 11,419,542 B2
(45) Date of Patent: Aug. 23, 2022

(54) SYSTEM AND METHOD FOR NON-APNEA SLEEP AROUSAL DETECTION

(71) Applicant: Tata Consultancy Services Limited, Mumbai (IN)

(72) Inventors: Tanuka Bhattacharjee, Kolkata (IN); Deepan Das, Kolkata (IN); Shahnawaz Alam, Kolkata (IN); Rohan Banerjee, Kolkata (IN); Anirban Dutta Choudhury, Kolkata (IN); Arpan Pal, Kolkata (IN); Achuth Rao Melavarige Venkatagiri, Bangalore (IN); Prasanta Kumar Ghosh, Bangalore (IN); Ayush Ranjan Lohani, Shibpur (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 510 days.

(21) Appl. No.: 16/578,270

(22) Filed: Sep. 20, 2019

(65) Prior Publication Data
US 2020/0093425 A1    Mar. 26, 2020

(30) Foreign Application Priority Data
Sep. 21, 2018    (IN) .............................. 201821035703

(51) Int. Cl.
*A61B 5/00*    (2006.01)
*G06K 9/62*    (2022.01)
(Continued)

(52) U.S. Cl.
CPC .......... *A61B 5/4818* (2013.01); *G06K 9/6227* (2013.01); *G06K 9/6268* (2013.01);
(Continued)

(58) Field of Classification Search
CPC .... A61B 5/4818; G06V 20/695; G06V 10/40; G06V 30/2552; G06K 9/6227; G06K 9/6268
See application file for complete search history.

(56) References Cited

U.S. PATENT DOCUMENTS 5,047,930 A * 9/1991 Martens ................. A61B 5/389
                                                       706/924
5,299,118 A * 3/1994 Martens ................. A61B 5/369
                                                       600/509
(Continued)

FOREIGN PATENT DOCUMENTS

ES           2684533        10/2018
KR    10-2015-0058344         5/2015
(Continued)

OTHER PUBLICATIONS

Shmiel et al., "Data mining techniques for detection of sleep arousals" (pp. 331-337) (Year: 2009).*
(Continued)

*Primary Examiner* — Manav Seth
(74) *Attorney, Agent, or Firm* — Finnegan, Henderson, Farabow, Garrett & Dunner LLP (57) ABSTRACT

Monitoring the quality of sleep of an individual is essential for ensuring one's overall well-being. The existing methods for non-apnea sleep arousal detection are manual. A system and method for the non-apnea sleep arousal detection has been provided. The method uses a feature engineering based binary classification approach for distinguishing non-apnea arousal and non-arousal. A training data set is prepared using a plurality of physiological signals. A plurality of features are derived from the training data set. Out of those only a set of features are selected for training a plurality of random forest classifier models. A test sample is then provided to the plurality of random forest classifier models in the instances
(Continued)

of fixed duration. This results in generation of prediction probabilities for each instances. The prediction probabilities are then used to predict the probabilities of non-apnea sleep arousal in the test sample.

11 Claims, 9 Drawing Sheets

(51) Int. Cl.
  *G06V 10/40* (2022.01)
  *G06V 20/69* (2022.01)
  *G06V 30/24* (2022.01)

(52) U.S. Cl.
  CPC .......... *G06V 10/40* (2022.01); *G06V 20/695* (2022.01); *G06V 30/2552* (2022.01)

(56) References Cited

U.S. PATENT DOCUMENTS

| | | | | |
|---|---|---|---|---|
| 7,025,729 | B2* | 4/2006 | de Chazal | G16Z 99/00 600/513 |
| 7,862,515 | B2* | 1/2011 | de Chazal | A61B 5/335 600/508 |
| 7,942,824 | B1* | 5/2011 | Kayyali | A61M 16/0003 128/204.26 |
| 8,545,416 | B1* | 10/2013 | Kayyali | A61B 5/0205 128/204.26 |
| 8,862,195 | B2* | 10/2014 | Homero | A61B 5/7264 600/323 |
| 8,880,207 | B2* | 11/2014 | Abeyratne | G06F 3/165 700/94 |
| 9,386,951 | B2* | 7/2016 | Sánchez | A61B 5/4818 |
| 9,730,632 | B1* | 8/2017 | Kayyali | A61B 5/0809 |
| 9,788,762 | B2* | 10/2017 | Auerbach | A61B 5/087 |
| 10,007,480 | B2* | 6/2018 | Abeyratne | G06F 3/165 |
| 10,321,871 | B2* | 6/2019 | Bandyopadhyay | G16H 50/20 |
| 2007/0032733 | A1* | 2/2007 | Burton | A61B 5/7264 600/509 |
| 2020/0346017 | A1* | 11/2020 | Caparso | A61B 5/4836 |
| 2022/0095952 | A1* | 3/2022 | Schipper | A61B 5/7282 |

FOREIGN PATENT DOCUMENTS

| | | |
|---|---|---|
| KR | 101601895 | 3/2016 |
| KR | 101868888 | 2/2018 |

OTHER PUBLICATIONS

Sugi et al., "Automatic EEG arousal detection for sleep apnea syndrome" (pp. 329-337) (Year: 2009).*

Liang et al., "Automatic Sleep Arousal Detection based on C-ELM" (pp. 376-382) (Year: 2015).*

Wallant et al., "Automatic artifacts and arousals detection in whole night sleep EEG recordings" (pp. 124-133) (Year: 2016).*

Chambon, S. et al. (Apr. 2018). "A deep learning architecture for temporal sleep stage classification using multivariate and multimodal time series," *IEEE Transaction on Neural Systems and Rehabilitation Engineering*, vol. 26, No. 4; pp. 1-12.

* cited by examiner

SYSTEM AND METHOD FOR NON-APNEA SLEEP AROUSAL DETECTION

PRIORITY CLAIM

This U.S. patent application claims priority under 35 U.S.C. § 119 to: India Application No. 201821035703 filed on 21 Sep. 2018. The entire contents of the aforementioned application are incorporated herein by reference.

TECHNICAL FIELD

The embodiments herein generally relate to the field of detection of sleeping disorders, and, more particularly, to a method and system for non-apnea sleep arousal detection.

BACKGROUND

The importance of sleep, for our overall health and well-being, is widely accepted. Inadequate sleep is associated with a wide range of negative outcomes including: impaired memory and learning, obesity, irritability, cardiovascular dysfunction, hypotension, diminished immune function and depression. Thus monitoring the quality of sleep of an individual is essential for ensuring one's overall well-being.

One of the more well-studied sleep disorders is obstructive sleep apnea hypopnea syndrome (or simply, apnea). Apneas are characterized by a complete collapse of the airway, leading to awakening, and consequent disturbances of sleep. While apneas are arguably the best understood of sleep disturbances, they are not the only cause of disturbance. Sleep arousals can also be spontaneous, result from teeth grinding, partial airway obstructions, or even snoring. These are referred as non-apnea sleep arousals.

Traditionally sleep disorder diagnosis is done at professional sleep laboratories by expert clinicians. They have to go through the tedious process of examining the polysomnographic recording of the entire sleep duration of the subject and manually annotating the presence or absence of any sleep disorder. Automatic algorithms are necessary to do away with this huge manual effort. Several successful efforts have been made towards the automatic detection of apnea disorders but the domain of non-apnea arousals is still not explored extensively.

SUMMARY

Embodiments of the present disclosure present technological improvements as solutions to one or more of the above-mentioned technical problems recognized by the inventors in conventional systems. For example, an embodiment herein provides a system for non-apnea sleep arousal detection. The system comprises an input module, a segmentation module, a preprocessor, a memory and a processor in communication with the memory. The input module obtains a plurality of physiological signals from a plurality of subjects to generate a training data set. The segmentation module segments the plurality of physiological signals into instances of a fixed duration. The preprocessor pre-processes the obtained instances of the plurality of physiological signals for removing noise, artefacts and sensor interference. The processor further comprises an extraction module, a ranking module, a feature selection module, a training module, a test sample preparation module, a prediction probability generation module, a mean calculation module, a stitching module and a smoothening module. The extraction module extracts a plurality of features from each instance of the pre-processed plurality of physiological signals. The ranking module ranks the plurality of features using a minimum redundancy maximum relevancy (mRMR) algorithm. The feature selection module selects a first set of features out of the plurality of features, wherein the first set of features is a fixed number of top ranked features out of the plurality of features. The training module trains a plurality of random forest classifier models using the selected first set of features, wherein each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers. The test sample preparation module is configured to: obtain the plurality of physiological signals from a test subject to generate a test sample, segment the plurality of physiological signals into instances of the same duration as the training data instances, pre-process the instances of the test sample for removing noise, artefacts and sensor interference, extract the selected first set of features from the instances of the pre-processed plurality of physiological signals, and provide the extracted first set of features of the instances of the test sample to the plurality of trained random forest classifier models for the detection of non-apnea sleep arousal. The prediction probability generation module generates a prediction probability by each of the plurality of classifiers for each instance of the test sample. The mean calculation module calculates a mean of the generated prediction probabilities of the plurality of classifiers for each instance to get a single prediction probability value for every particular instance of the test sample. The stitching module stitches the prediction probabilities of all the instances of the test sample to generate a time series of the prediction probability values. The smoothening module smoothens the stitched prediction probability values to get rid of spurious detections, wherein the smoothened prediction probability value time series is used as the probabilities of non-apnea sleep arousal in the test sample.

In another aspect the embodiment here provides a method for non-apnea sleep arousal detection. Initially, a plurality of physiological signals are obtained from a plurality of subjects to generate a training data set. In the next step, the plurality of physiological signals are segmented into instances of a fixed duration. The obtained instances of the plurality of physiological signals are then pre-processed for removing noise, artefacts and sensor interference. In the next step, a plurality of features are extracted from each instance of the pre-processed plurality of physiological signals. The plurality of features are then ranked using a minimum redundancy maximum relevancy (mRMR) algorithm. In the next step, a first set of features are selected out of the plurality of features, wherein the first set of features is a fixed number of top ranked features out of the plurality of features. In the next step, a plurality of random forest classifier models are trained using the selected first set of features, wherein each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers. In the next step, the plurality of physiological signals are obtained from a test subject to generate a test sample. In the next step, the plurality of physiological signals of the test sample are segmented into instances of the same duration as training dataset. The instances of the plurality of physiological signals of the test sample are then pre-processed for removing noise, artefacts and sensor interference. In the next step, the selected first set of features are extracted from the instances of the pre-processed plurality of physiological signals. The extracted first set of features of the instances of the test sample are then provided to the plurality of trained random forest classifier models for the detection of non-apnea sleep arousal. In the next step, a prediction probability by each of the plurality of classifiers for each instance of the test sample is generated. In the next step, a mean of the generated prediction probabilities of the plurality of classifiers is calculated for each instance to get a single prediction probability value for every particular instance of the test sample. In the next step, the prediction probabilities of all the instances of the test sample are stitched to generate a time series of the prediction probability values. And finally, the stitched prediction probability values are smoothened to get rid of spurious detections, wherein the smoothened prediction probability values time series is used as the probabilities of non-apnea sleep arousal in the test sample.

In another aspect the embodiment here provides one or more non-transitory machine readable information storage mediums comprising one or more instructions which when executed by one or more hardware processors cause non-apnea sleep arousal detection. Initially, a plurality of physiological signals are obtained from a plurality of subjects to generate a training data set. In the next step, the plurality of physiological signals are segmented into instances of a fixed duration. The obtained instances of the plurality of physiological signals are then pre-processed for removing noise, artefacts and sensor interference. In the next step, a plurality of features are extracted from each instance of the pre-processed plurality of physiological signals. The plurality of features are then ranked using a minimum redundancy maximum relevancy (mRMR) algorithm. In the next step, a first set of features are selected out of the plurality of features, wherein the first set of features is a fixed number of top ranked features out of the plurality of features. In the next step, a plurality of random forest classifier models are trained using the selected first set of features, wherein each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers. In the next step, the plurality of physiological signals is obtained from a test subject to generate a test sample. In the next step, the plurality of physiological signals of the test sample are segmented into instances of the same duration as training dataset. The instances of the plurality of physiological signals of the test sample are then pre-processed for removing noise, artefacts and sensor interference. In the next step, the selected first set of features are extracted from the instances of the pre-processed plurality of physiological signals. The extracted first set of features of the instances of the test sample are then provided to the plurality of trained random forest classifier models for the detection of non-apnea sleep arousal. In the next step, a prediction probability by each of the plurality of classifiers for each instance of the test sample is generated. In the next step, a mean of the generated prediction probabilities of the plurality of classifiers is calculated for each instance to get a single prediction probability value for every particular instance of the test sample. In the next step, the prediction probabilities of all the instances of the test sample are stitched to generate a time series of the prediction probability values. And finally, the stitched prediction probability values are smoothened to get rid of spurious detections, wherein the smoothened prediction probability values time series is used as the probabilities of non-apnea sleep arousal in the test sample.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method.

Figure 1:
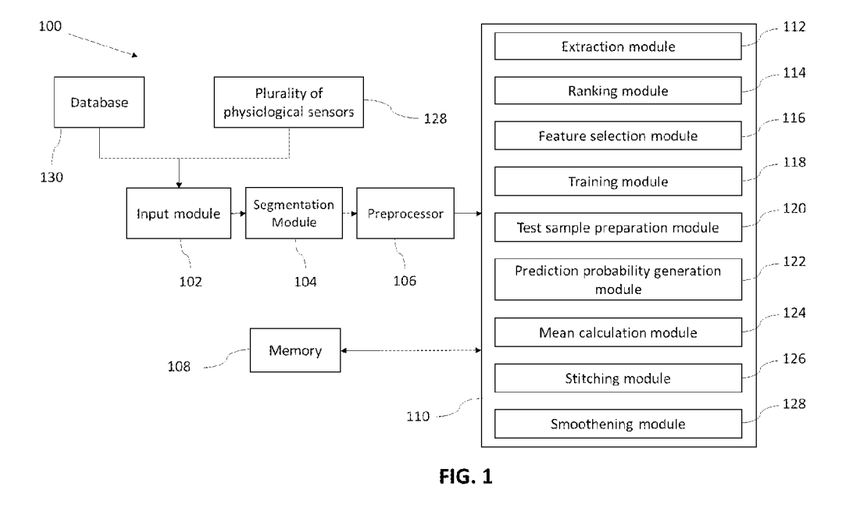
FIG. 1 illustrates a block diagram of a system for detection of non-apnea sleep arousal according to an embodiment of the present disclosure.

According to an embodiment of the disclosure, a system 100 for non-apnea sleep arousal detection is shown in the block diagram of FIG. 1. The system 100 is configured to automatically detect the presence of non-apnea sleep arousals in the sleeping pattern of a person. The proposed approach of automatic non-apnea arousal detection helps avoid the huge manual effort involved in the process. The system 100 is using an algorithm for distinguishing non-apnea arousals from sound sleep by automatic analysis of polysomnographic signals captured from the person. The non-apnea arousals may include, but not limited to respiratory effort related arousal (RERA), bruxism, snoring etc.

According to an embodiment of the disclosure, the system 100 comprises an input module 102, a segmentation module 104, a pre-processor 106, a memory 108 and a processor 110 as shown in the block diagram of FIG. 1. The processor 110 is in communication with the memory 108. The processor 110 is configured to execute a plurality of algorithms stored in the memory 108. The processor 110 further includes a plurality of modules for performing various functions. The processor 110 may include an extraction module 112, a ranking module 114, a feature selection module 116, a training module 118, a test sample preparation module 120, a prediction probability generation module 122, a mean calculation module 124, a stitching module 126 and a smoothening module 128.

According to an embodiment of the disclosure, the input module 102 is configured to provide an input to the processor 110. The input module 102 is configured to obtain a plurality of physiological signals to generate a training dataset. The plurality of physiological signals can be obtained either from a plurality of physiological sensors 128 or from a database 130. The plurality of physiological signals are obtained from a plurality of subjects. The plurality of physiological signals may include 6-channel electroencephalography (EEG), single channel electrooculography (EOG), 3-channel electromyography (EMG), single-lead electrocardiography (EKG), respiratory airflow and oxygen saturation (SaO2). The input module 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

According to an embodiment of the disclosure, the system 100 comprises the segmentation module 104. The segmentation module 104 is configured to segment the plurality of physiological signals into instances of a fixed duration. In the present example, a duration of 20 s with 10% overlap is chosen as the length of an instance.

Figure 3:
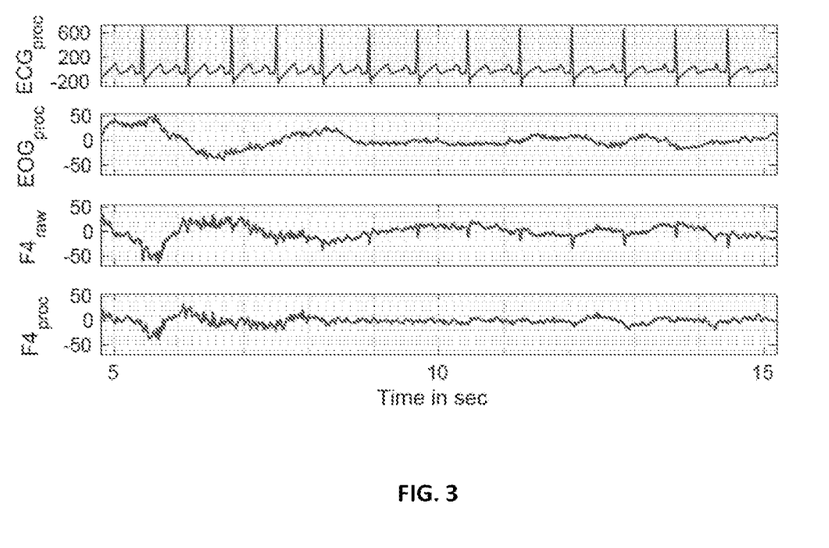
FIG. 3 shows a graphical representation of EEG waveform recorded, from the F4 position, before (F4raw) and after (F4proc) adaptive RLS filtering was employed to remove ECG and EOG contamination according to an embodiment of the disclosure.

The system 100 also comprises the preprocessor 106. The preprocessor 106 is configured to pre-process the instances of the plurality of physiological signals for removing noise, artefacts and sensor interference. The pre-processing is performed before providing the plurality of physiological signals to the processor 110. All channels are filtered appropriately, according to the requirements of the individual sensors. ECG signal might contaminate EEG, EOG and Chin-EMG channels as additive noise. EOG also can contaminate the frontal EEG channels similarly. To deal with this, adaptive Recursive Least Squares (RLS) filtering technique is used to first remove ECG from EOG and Chin-EMG, then remove both ECG and decontaminated EOG from EEG. FIG. 3 shows the outcome of pre-processing on EEG.

According to an embodiment of the disclosure, the processor 110 comprises the extraction module 112. The extraction module 112 is configured to extract a plurality of features from each pre-processed instance. Discovering features capable of distinguishing the concerned classes is the most important part of any conventional approach of handling classification problems. In the present disclosure, all 13 physiological signals of the given polysomnographic recordings are used to extract features which may correlate to the non-apnea arousal/non-arousal labels. The considered features can be classified broadly into two categories, as follows.

Domain/Sensor independent generic features: A set of 392 generic features is derived from each signal channel. These features include various statistical properties (e.g. mean, variance, skewness, kurtosis, Box-Pierce statistics, Hurst exponent) of the time domain signal, its Fast Fourier Transform (FFT) coefficients and Discrete Wavelet Transform (DWT) coefficients. Other spectral features like centroid, roll off, flux and different entropy measures (e.g. Shannon, Renyi, Tsallis) are also considered.

Domain/Sensor specific features: A total of 1044 features spread across the 13 channels are computed. These comprise asymmetry features from 5 standard frequency bands (e.g. delta, theta, alpha, beta and gamma) of the 6 EEG channels, morphological and heart rate variability features from ECG, visibility graph based features from ECG, EEG and Cardio-Respiratory Interaction (CRI) time-series, breathing rate variability features from Chest, Abdomen EMG and Airflow. Morphologies of the breathing cycles, breath-by-breath correlation, phase relation between Chest and Abdomen EMG are also explored.

According to an embodiment of the disclosure, the processor 110 also comprises the ranking module 114 and the feature selection module 116. The ranking module 114 is configured to rank the plurality of features using a minimum redundancy maximum relevancy (mRMR) algorithm. The feature selection module 116 is configured to select a first set of features out of the plurality of features, wherein the first set of features is a fixed top ranked features out of the plurality of features. Feature selection helps in discarding the irrelevant and redundant features, thereby lowering both bias and variance of the proposed algorithm.

Figure 4:
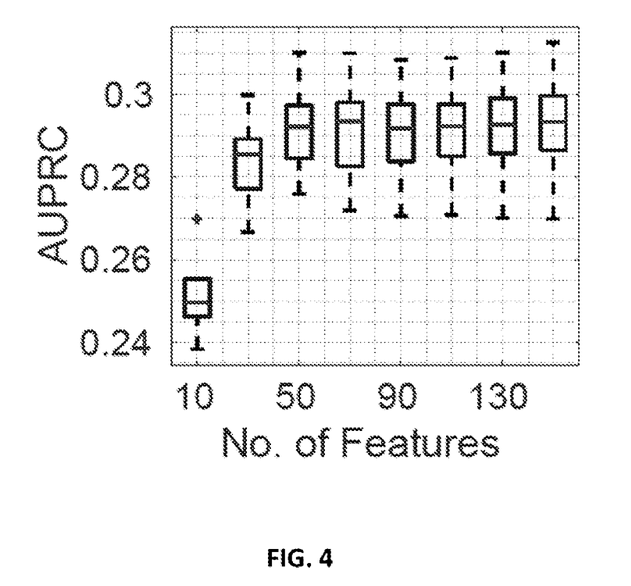
FIG. 4 is graphical representation of 5-fold performance (Area under Precision-Recall Curve—AUPRC) evaluation for an increasing feature set, ranked using mRMR technique according to an embodiment of the disclosure.
Figure 5:
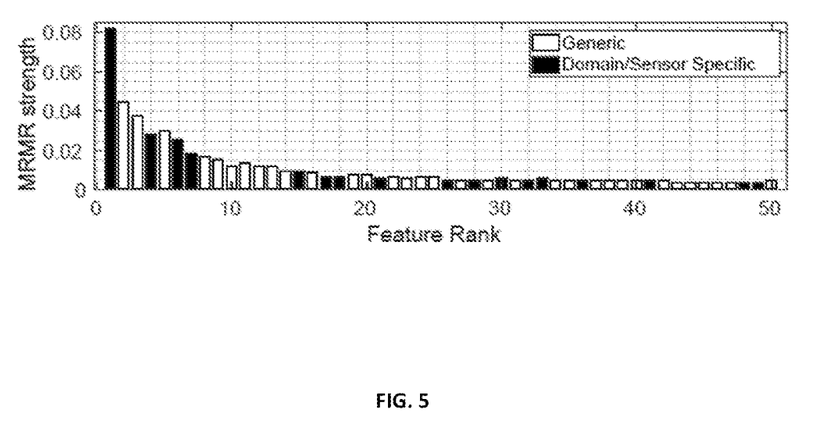
FIG. 5 shows distribution of top 50 features across generic and domain specific features according to an embodiment of the disclosure.
Figure 6:
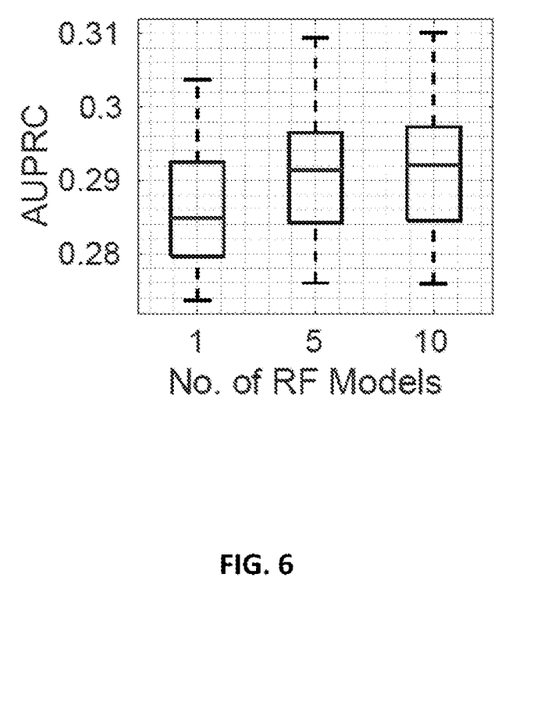
FIG. 6 shows variation in 5-fold AUPRC when different number of trained models are used and their mean probability is taken as output for a tested instance according to an embodiment of the disclosure.

FIG. 4 shows the variation of AUPRC over 5-folds of cross-validation with the increase in the number of selected features. The data was partitioned such that recordings from the same subject never belonged to both train and test folds. It can be seen that the best bias-variance value pair is obtained while using the top 50 features. Thus, top 50 features were selected as the first set of features. With this many number of features, any test data of about 8 hours duration would need approximately $5*10^{12}$ CPU instructions at most for complete execution. FIG. 5 shows the strengths of the top 50 features selected. Among these, 34% features come from the domain/sensor specific category. The distribution of the selected features over the different physiological signals is depicted in Table 1. It shows that Chin EMG, Abdomen EMG, Airflow and SaO2 are the most important indicators of non-apnea arousal.

TABLE 1

Distribution of top 50 features across sensors and across generic and domain/sensor specific varieties

| Physiological signal | | Generic features selected | Sensor specific features selected | Total |
|---|---|---|---|---|
| EEG | F3-M2 | 2 | — | 2 |
| | F4-M1 | 1 | 1 | 2 |
| | C3-M2 | 1 | — | 1 |
| | C4-M1 | 2 | — | 2 |
| | O1-M2 | 1 | — | 1 |
| | O2-M1 | — | 1 | 1 |
| | EOG | 3 | — | 3 |
| EMG | Chin | 4 | 2 | 6 |
| | Abdomen | 5 | 3 | 8 |
| | Chest | 2 | 2 | 4 |
| | Airflow | 6 | — | 6 |
| | SaO2 | 6 | 1 | 7 |
| | ECG | — | 5 | 5 |
| | Multi-signal | — | 2 | 2 |
| | Total | 33 | 17 | 50 |

According to an embodiment of the disclosure, the processor 110 further comprises the training module 118. The training module 118 is configured to train a plurality of random forest classifier models using the selected first set of features. Each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers.

In the present embodiment, the random forest model is chosen as the classifier. However, training it using the unbalanced data leads to most testing instances being classified into the majority class. On the other hand, dropping major class instances in order to train the model on balanced data produces a more balanced outcome. But this means that only a small fraction of the major class is used in training. To have the best of both worlds, an approach using multiple trained models is used. In the present example, 10 random forest classifiers are trained. All the minority class in training dataset are fed to every classifier. The majority class is balanced per classifier and is mutually exclusive with the majority class instances used to train any other classifier. Thus, both a balanced training and a greater coverage of majority class are ensured. While labelling a test instance, the mean of the output probabilities of belonging to non-apnea arousal class, of all 10 models, is considered as the final posteriori probability. The advantage of using multiple fair models, over a single such model, is demonstrated in FIG. 6.

According to an embodiment of the disclosure, the processor 110 also comprises the test sample preparation module 120. The test sample preparation module 120 is configured to obtain the plurality of physiological signals from a test subject to generate a test sample. The obtained test sample is used to detect the non-apnea arousal after some preparation. Before that, the plurality of physiological signals of the test sample are segmented into instances of the same duration as the training dataset signals. The instances are then pre-processed for removing noise, artefacts and sensor interference. The selected first set of features are then extracted from the instances of the pre-processed plurality of physiological signals. The extracted first set of features of the test sample instances are then provided to the plurality of trained random forest classifier models for the detection of non-apnea sleep arousal.

According to an embodiment of the disclosure, the processor 110 also comprises the prediction probability generation 122 and the mean calculation module 124. The prediction probability generation module 122 is configured to generate a prediction probability by each of the plurality of classifiers for each instance of the test sample. The mean calculation module 124 is configured to calculate a mean of the generated prediction probabilities of the plurality of classifiers for each instance to get a single prediction probability value for every particular instance of the test sample.

Figure 7:
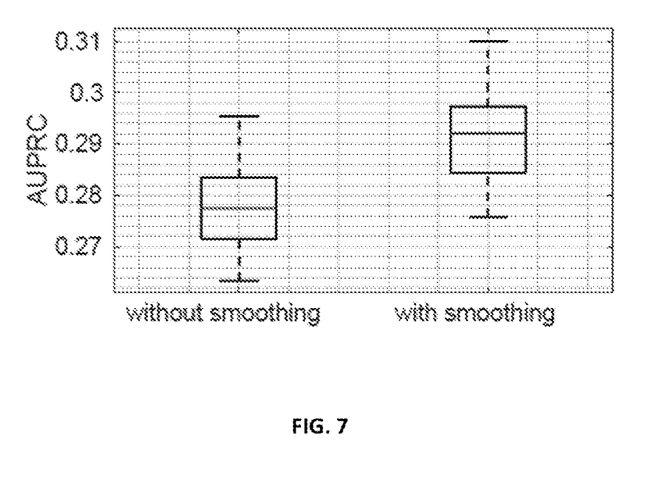
FIG. 7 shows variation in 5-fold AUPRC with and without smoothing of the predicted probability time-series according to an embodiment of the disclosure.

According to an embodiment of the disclosure, the processor 110 also comprises the stitching module 126 and the smoothening module 128. Using the above method, each 20-second test instance receives a single output label. The stitching module 126 is configured to stitch the prediction probabilities of all the instances of the test sample to generate a time series of the prediction probability values. The obtained probability time-series is at par with the annotation time-series provided. The 10% overlap between consecutive signal segments is handled and is expected to avoid sharp transitions between segments. The smoothening module 128 is configured to smoothen the stitched prediction probability values to get rid of spurious detections. The smoothened prediction probability values time series is used as the probabilities of non-apnea sleep arousal in the test sample. The prediction probability time-series is smoothened using a 5-second moving average filter. Performance gain from smoothing is shown in FIG. 7.

Figure 2A:
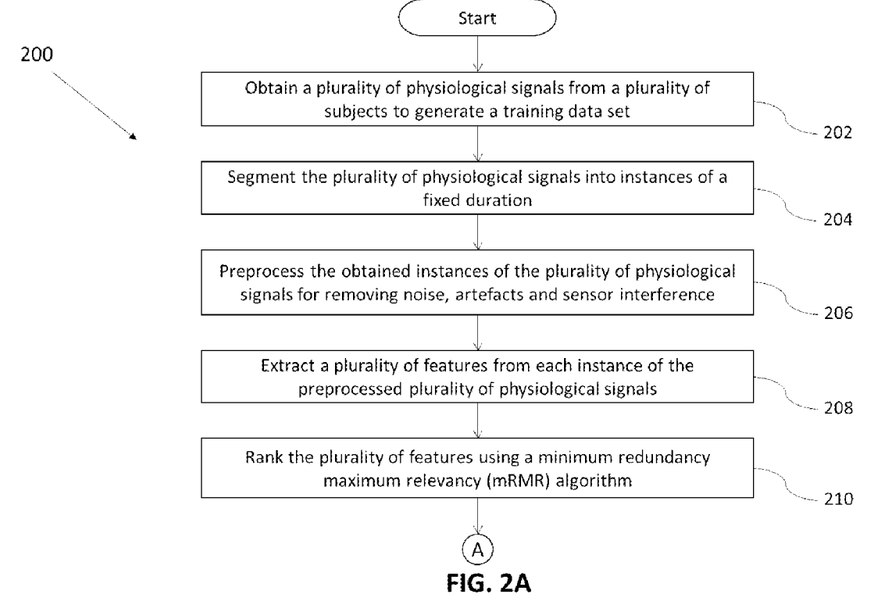
FIG. 2A-2C is a flowchart illustrating the steps involved in detection of non-apnea sleep arousal according to an embodiment of the present disclosure.
Figure 2B:
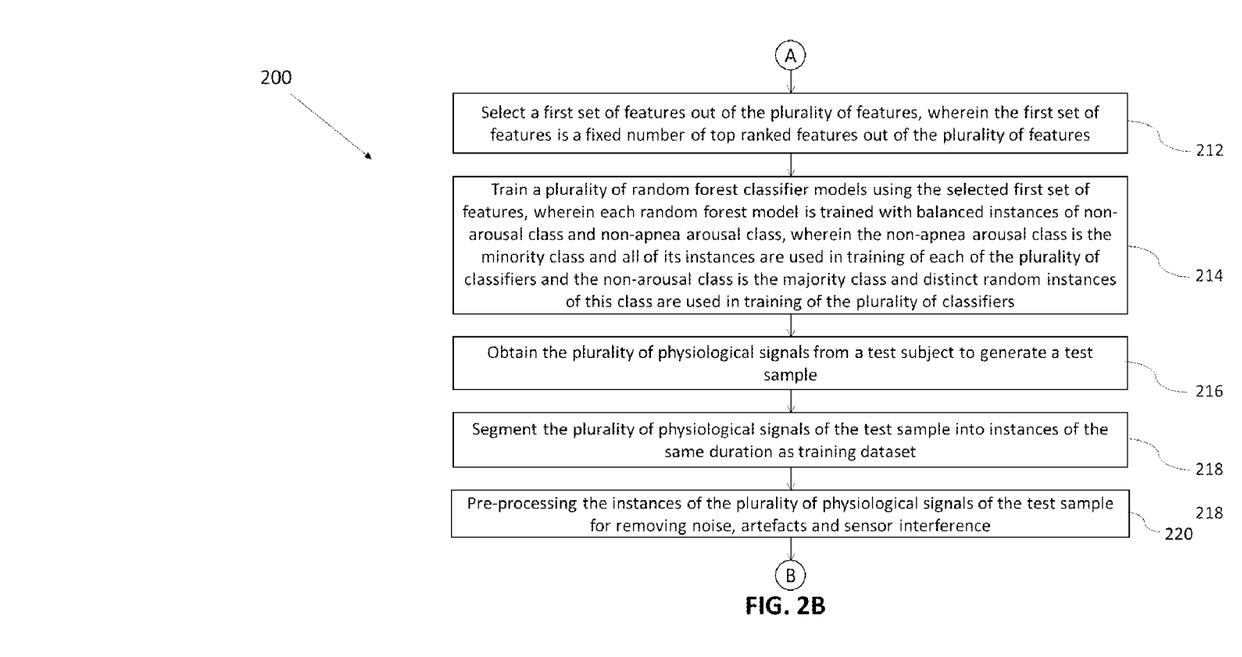

In operation, a flowchart 200 illustrating the steps of non-apnea sleep arousal detection is shown in FIG. 2A-2B. Initially at step 202, the plurality of physiological signals are obtained from the plurality of subjects to generate the training data set. The plurality of physiological signals may be either obtained from the plurality of physiological sensors 128 or from the database 130. At step 204, the plurality of physiological signals are segmented into instances of a fixed duration. At step 206, the obtained instances of the plurality of physiological signals are pre-processed for removing noise, artefacts and sensor interference.

In the next step 208, the plurality of features are extracted from each instance of the pre-processed plurality of physiological signals, wherein the plurality of features comprising the set of generic features and the set of domain specific features. At step 210, the plurality of features are ranked using a minimum redundancy maximum relevancy (mRMR) algorithm. Followed by at step 212, the first set of features are selected out of the plurality of features. The first set of features are a fixed top ranked features out of the plurality of features. In the present example 50 top ranked features are selected as the first set of features.

In the next step 214, the plurality of random forest classifier models are trained using the selected first set of features. Each random forest model is trained with balanced instances of non-arousal class and non-apnea arousal class. The non-apnea arousal class is the minority class and all of its instances are used in training of each of the plurality of classifiers and the non-arousal class is the majority class and distinct random instances of this class are used in training of the plurality of classifiers.

Figure 2C:
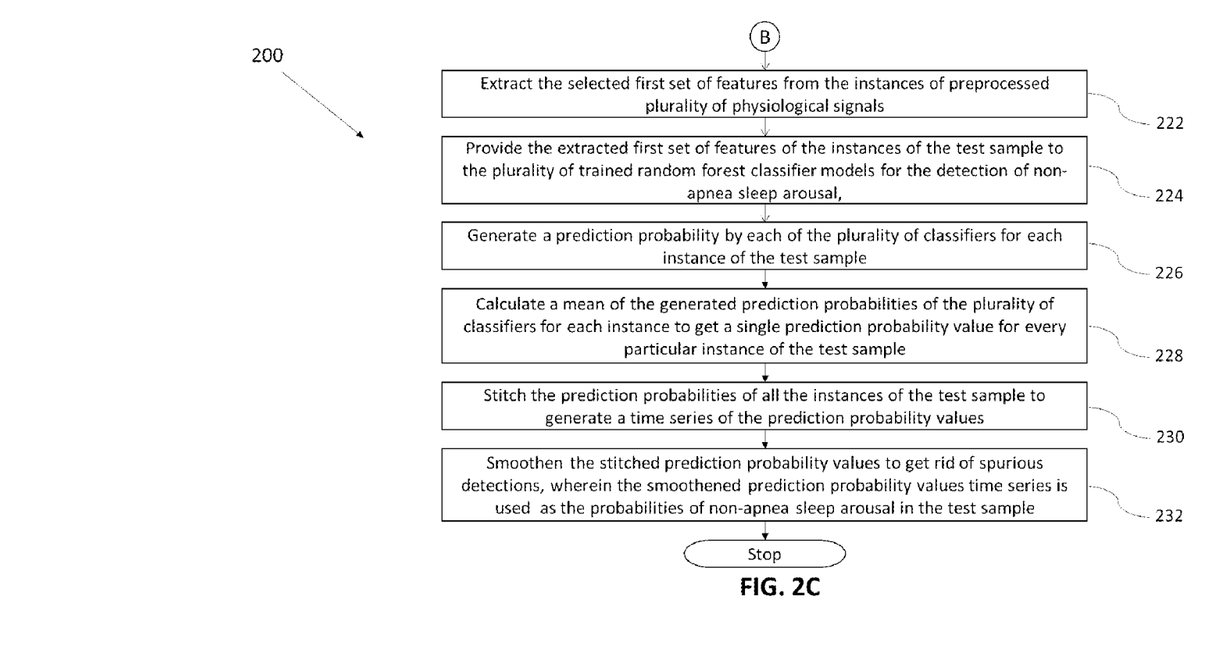

In the next step 216, the plurality of physiological signals from the test subject is obtained to generate the test sample. At step 218, the plurality of physiological signals of the test sample are segmented into instances of the same duration as training dataset. At step 220, the instances of the plurality of physiological signals of the test sample are pre-processed for removing noise, artefacts and sensor interference. At step 222, the selected first set of features are then extracted from the instances of the pre-processed plurality of physiological signals. At step 224, the extracted first set of features of the instances of the test sample are provided to the plurality of trained random forest classifier models for the detection of non-apnea sleep arousal.

In the next step 226, the prediction probability is generated by each of the plurality of classifiers for each instance of the test sample. Further at step 228, the mean of the generated prediction probabilities of the plurality of classifiers is calculated for each instance to get a single prediction probability value for every particular instance of the test sample. In the next step 230, the prediction probabilities of all the instances of the test sample are stitched to generate a time series of the prediction probability values. And finally at step 232, the stitched prediction probability values are smoothened to get rid of spurious detections, wherein the smoothened prediction probability values time series is used as the probabilities of non-apnea sleep arousal in the test sample.

According to an embodiment of the disclosure, the system 100 for non-apnea sleep arousal detection can also be explained with the help of following example. In the present example, the data were contributed by the Massachusetts General Hospitals (MGH) Computational Clinical Neurophysiology Laboratory (CCNL), and the Clinical Data Animation Laboratory (CDAC). The dataset includes 1,985 subjects who were monitored at an MGH sleep laboratory for the diagnosis of sleep disorders. The data were partitioned into balanced training (n=994), and test sets (n=989).

The sleep stages of the subjects were annotated by clinical staff at the MGH according to the American Academy of Sleep Medicine (AASM) manual for the scoring of sleep. More specifically, the following six sleep stages were annotated in 30 second contiguous intervals: wakefulness, stage 1, stage 2, stage 3, rapid eye movement (REM), and undefined. Certified sleep technologists at the MGH also annotated waveforms for the presence of arousals that interrupted the sleep of the subjects. The annotated arousals were classified as either: spontaneous arousals, respiratory effort related arousals (RERA), bruxisms, hypoventilations, hypopneas, apneas (central, obstructive and mixed), vocalizations, snores, periodic leg movements, Cheyne-Stokes breathing or partial airway obstructions.

The subjects had a variety of physiological signals recorded as they slept through the night including: 6-channel electroencephalography (EEG), single channel electrooculography (EOG), 3-channel electromyography (EMG), single-lead electrocardiography (EKG), respiratory airflow and oxygen saturation (SaO2). Excluding SaO2, all signals were sampled to 200 Hz and were measured in microvolts. For analytic convenience, SaO2 was resampled to 200 Hz, and was measured as a percentage.

Data Preparation

For every subject, signals from every channel was split into segments of 20 second duration, with 10% overlap between 2 consecutive segments. In case of training data, the corresponding annotation time-series was replaced by a single label per 20-second segment. If the entire segment was annotated as non-arousal (nA), it was replaced by a single nA label. On the other hand, if at least 80% duration of the segment was annotated as non-apnea or target arousal (tA), it was replaced by a single tA label. Ratio of classes nA to tA was around 16:1. Labeling segments, with non-apnea arousal throughout, as class tA' was also tried. But, in that approach, ratio of classes nA to tA' turned out to be greater than 20:1. Thus, the approach slightly improves the class imbalance in favor of the minority class.

Further, the plurality of classifiers were generated as per the above mentioned approach. The results were obtained as follows:

The performance of the present approach during 5-fold cross-validation over the training data is detailed in Table 2. It should be noted that as more subjects are evaluated, the gross AUPRC for all tested subjects first peaks to 0.45 for around 20 subjects, comes down to 0.30 for 100 subjects and asymptotically approaches 0.29 as subjects increase. The hidden test set produced an AUPRC of 0.29, which is in keeping with the internal cross-validation results as shown in Table 2 below.

TABLE 2

|  | Fold1 | Fold2 | Fold3 | Fold4 | Fold5 |
|---|---|---|---|---|---|
| AUPRC | 0.287 | 0.292 | 0.276 | 0.310 | 0.293 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein solves the problems related to monitoring the quality of sleep in an individual. The disclosure provides a method and system for non-apnea sleep arousal detection.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for non-apnea sleep arousal detection, the method comprising a processor implemented steps of:
    obtaining a plurality of physiological signals from a plurality of subjects to generate a training data set;
    segmenting the plurality of physiological signals into instances of a fixed duration;
    pre-processing the obtained instances of the plurality of physiological signals for removing noise, artefacts and sensor interference;
    extracting a plurality of features from each instance of the pre-processed plurality of physiological signals;
    ranking the plurality of features using a minimum redundancy maximum relevancy (mRMR) algorithm;
    selecting a first set of features out of the plurality of features, wherein the first set of features is a fixed number of top ranked features out of the plurality of features;
    training a plurality of random forest classifier models using the selected first set of features, wherein each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers;
    obtaining the plurality of physiological signals from a test subject to generate a test sample;
    segmenting the plurality of physiological signals of the test sample into instances of the same duration as training dataset;
    pre-processing the instances of the plurality of physiological signals of the test sample for removing noise, artefacts and sensor interference;
    extracting the selected first set of features from the instances of the pre-processed plurality of physiological signals;
    providing the extracted first set of features of the instances of the test sample to the plurality of trained random forest classifier models for the detection of non-apnea sleep arousal;
    generating a prediction probability by each of the plurality of classifiers for each instance of the test sample;
    calculating a mean of the generated prediction probabilities of the plurality of classifiers for each instance to get a single prediction probability value for every particular instance of the test sample;
    stitching the prediction probabilities of all the instances of the test sample to generate a time series of the prediction probability values; and
    smoothening the stitched prediction probability values to get rid of spurious detections, wherein the smoothened prediction probability values time series is used as the probabilities of non-apnea sleep arousal in the test sample.

2. The method of claim 1 wherein the plurality of physiological signals are captured using a plurality of physiological sensors.

3. The method of claim 2, wherein the plurality of physiological sensors comprises an electroencephalogram (EEG), an electrocardiogram (ECG) an elctro-occulogram (EOG), electromyogram (EMG), an air flow sensor and an oxygen saturation measurement (SaO2) device.

4. The method of claim 1, wherein the plurality of features comprising a set of generic features and a set of domain specific features.

5. The method of claim 1, wherein the fixed number of top ranked features is selected based on a value of performance bias and variance.

6. The method of claim 1, wherein the instances of the fixed duration are provided with an overlap of 10% to avoid sharp transition between instances.

7. The method of claim 1, wherein the step of smoothening is performed using a 5-second moving average filter.

8. The method of claim 1, wherein the plurality of physiological signals for generating the training dataset can also be obtained from a database.

9. A system for non-apnea sleep arousal detection, the system comprises:
    a memory; and
    a processor in communication with the memory, the processor is configured to:
        obtain a plurality of physiological signals from a plurality of subjects to generate a training data set;
        segment the plurality of physiological signals into instances of a fixed duration;
        pre-process the obtained instances of the plurality of physiological signals for removing noise, artefacts and sensor interference;
        extract a plurality of features from each instance of the pre-processed plurality of physiological signals;
        rank the plurality of features using a minimum redundancy maximum relevancy (mRMR) algorithm;
        select a first set of features out of the plurality of features, wherein the first set of features is a fixed number of top ranked features out of the plurality of features;
        train a plurality of random forest classifier models using the selected first set of features, wherein the random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers;
        obtain the plurality of physiological signals from a test subject to generate a test sample,
        segment the plurality of physiological signals of the test sample into instances of the same duration as training dataset;
        pre-process the instances of the plurality of physiological signals of the test sample for removing noise, artefacts and sensor interference,
        extract the selected first set of features from the instances of the pre-processed plurality of physiological signals, and provide the extracted first set of features of the instances of the test sample to the plurality of trained random forest classifier models for the detection of non-apnea sleep arousal;
generate a prediction probability by each of the plurality of classifiers for each instance of the test sample;
calculate a mean of the generated prediction probabilities of the plurality of classifiers for each instance to get a single prediction probability value for every particular instance of the test sample;
stitch the prediction probabilities of all the instances of the test sample to generate a time series of the prediction probability values; and
smoothen the stitched prediction probability values to get rid of spurious detections, wherein the smoothened prediction probability values time series is used as the probabilities of non-apnea sleep arousal in the test sample.

10. The system of claim 9 further comprising a plurality of physiological sensors to capture the plurality of physiological signals.

11. One or more non-transitory machine readable information storage mediums comprising one or more instructions which when executed by one or more hardware processors cause identification of key driver responsible for bringing a change in a microbial population, the instructions cause:
obtaining a plurality of physiological signals from a plurality of subjects to generate a training data set;
segmenting the plurality of physiological signals into instances of a fixed duration;
pre-processing the obtained instances of the plurality of physiological signals for removing noise, artefacts and sensor interference;
extracting a plurality of features from each instance of the pre-processed plurality of physiological signals;
ranking the plurality of features using a minimum redundancy maximum relevancy (mRMR) algorithm;
selecting a first set of features out of the plurality of features, wherein the first set of features is a fixed number of top ranked features out of the plurality of features;
training a plurality of random forest classifier models using the selected first set of features, wherein each random forest model is trained with balanced instances of non-arousal class and non-apnea arousal class, wherein the non-apnea arousal class is the minority class and all of its instances are used in training of each of the plurality of classifiers and the non-arousal class is the majority class and distinct random instances of this class are used in training of the plurality of classifiers;
obtaining the plurality of physiological signals from a test subject to generate a test sample;
segmenting the plurality of physiological signals of the test sample into instances of the same duration as training dataset;
pre-processing the instances of the plurality of physiological signals of the test sample for removing noise, artefacts and sensor interference;
extracting the selected first set of features from the instances of the pre-processed plurality of physiological signals;
providing the extracted first set of features of the instances of the test sample to the plurality of trained random forest classifier models for the detection of non-apnea sleep arousal;
generating a prediction probability by each of the plurality of classifiers for each instance of the test sample;
calculating a mean of the generated prediction probabilities of the plurality of classifiers for each instance to get a single prediction probability value for every particular instance of the test sample;
stitching the prediction probabilities of all the instances of the test sample to generate a time series of the prediction probability values; and
smoothening the stitched prediction probability values to get rid of spurious detections, wherein the smoothened prediction probability values time series is used as the probabilities of non-apnea sleep arousal in the test sample.

* * * * *